US009307931B2

(12) United States Patent
Byrd et al.

(10) Patent No.: US 9,307,931 B2
(45) Date of Patent: Apr. 12, 2016

(54) MULTIPLE SHELL CONSTRUCTION TO EMULATE CHAMBER CONTRACTION WITH A MAPPING SYSTEM

(75) Inventors: Israel A. Byrd, Richfield, MN (US); Dale Just, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1284 days.

(21) Appl. No.: 12/347,216

(22) Filed: Dec. 31, 2008

(65) Prior Publication Data
US 2010/0168550 A1    Jul. 1, 2010

(51) Int. Cl.
*A61B 5/05*  (2006.01)
*A61B 5/02*  (2006.01)
*A61B 5/107*  (2006.01)
*A61B 5/00*  (2006.01)
(Continued)

(52) U.S. Cl.
CPC ............. *A61B 5/1076* (2013.01); *A61B 5/0006* (2013.01); *A61B 5/0422* (2013.01); *A61B 5/063* (2013.01); *A61B 5/6885* (2013.01); *A61B 5/7289* (2013.01); *A61B 5/04011* (2013.01); *A61B 5/0428* (2013.01); *A61B 5/0452* (2013.01); *A61B 5/04085* (2013.01); *A61B 5/06* (2013.01)

(58) Field of Classification Search
CPC .. A61B 5/04011; A61B 5/1076; A61B 5/063; A61B 5/7289; A61B 5/06; A61B 5/0428; A61B 5/0006; A61B 5/0452
USPC ................................................ 607/407, 508
See application file for complete search history.

(56) References Cited

U.S. PATENT DOCUMENTS 5,391,199 A  *  2/1995  Ben-Haim ................. 607/122
6,233,476 B1     5/2001  Strommer et al.
(Continued)

FOREIGN PATENT DOCUMENTS

EP   1070480    1/2001
EP   2757528    7/2014
(Continued)

OTHER PUBLICATIONS

U.S. Appl. No. 09/107,371, filed Jun. 30, 1998 for "Chamber Mapping System".
(Continued)

Primary Examiner — Niketa Patel
Assistant Examiner — Lindsey G Hankins
(74) Attorney, Agent, or Firm — Dykema Gossett PLLC (57) ABSTRACT

A system for constructing multiple shells (electronic models) indicative of the geometry and/or volume of a bodily lumen, such as a heart chamber, is configured to collect a plurality of location data points as the electrode is swept within the chamber. Each of the collected data points has an associated measured cardiac phase at which such point was acquired. The system is configured to segregate the collected electrode locations into sets based on the phase. Each set is characterized by a particular, associated phase of its constituent electrode locations. The system is configured to generate, for each set, a respective shell that will represent the chamber at the associated phase. The shells, once constructed, may be used for or in connection with a variety of diagnostic, mapping, and/or therapeutic procedures. The system is also configured to verify that the electrode is in contact with the heart tissue before using the collected data point in the shell construction (e.g., using a phase angle parameter to verify contact).

30 Claims, 7 Drawing Sheets

(51) Int. Cl.
*A61B 5/042* (2006.01)
*A61B 5/04* (2006.01)
*A61B 5/0428* (2006.01)
*A61B 5/0452* (2006.01)
*A61B 5/0408* (2006.01)
*A61B 5/06* (2006.01)

(56) References Cited

U.S. PATENT DOCUMENTS

| | | | |
|---|---|---|---|
| 6,301,496 B1* | 10/2001 | Reisfeld | 600/407 |
| 6,609,027 B2* | 8/2003 | Kroll et al. | 607/9 |
| 6,633,686 B1 | 10/2003 | Bakircioglu et al. | |
| 6,728,562 B1 | 4/2004 | Budd et al. | |
| 6,751,492 B2* | 6/2004 | Ben-Haim | 600/374 |
| 6,978,168 B2 | 12/2005 | Beatty et al. | |
| 7,197,354 B2 | 3/2007 | Sobe | |
| 7,263,397 B2 | 8/2007 | Hauck et al. | |
| 7,276,064 B2 | 10/2007 | Paul et al. | |
| 7,338,486 B2 | 3/2008 | Sliwa et al. | |
| 7,386,339 B2 | 6/2008 | Strommer et al. | |
| 7,505,809 B2 | 3/2009 | Strommer et al. | |
| 7,697,973 B2 | 4/2010 | Strommer et al. | |
| 7,881,769 B2 | 2/2011 | Sobe | |
| 8,016,764 B1 | 9/2011 | Shelchuk | |
| 2003/0093067 A1 | 5/2003 | Panescu | |
| 2003/0233039 A1 | 12/2003 | Sho et al. | |
| 2005/0154282 A1 | 7/2005 | Li et al. | |
| 2006/0245536 A1 | 11/2006 | Boing et al. | |
| 2007/0073179 A1 | 3/2007 | Afonso et al. | |
| 2007/0100332 A1 | 5/2007 | Paul et al. | |
| 2007/0106146 A1 | 5/2007 | Altmann et al. | |
| 2007/0181139 A1 | 8/2007 | Hauck | |
| 2007/0244479 A1 | 10/2007 | Beatty et al. | |
| 2007/0270705 A1 | 11/2007 | Starks | |
| 2008/0009758 A1 | 1/2008 | Voth | |
| 2008/0091193 A1 | 4/2008 | Kauphusman et al. | |
| 2009/0163904 A1 | 6/2009 | Miller et al. | |
| 2009/0171345 A1 | 7/2009 | Miller et al. | |
| 2010/0268059 A1 | 10/2010 | Ryu et al. | |
| 2011/0243401 A1 | 10/2011 | Zabair et al. | |
| 2012/0184863 A1 | 7/2012 | Harlev et al. | |
| 2013/0222415 A1 | 8/2013 | Vilsmeier | |
| 2013/0272592 A1 | 10/2013 | Eichler et al. | |
| 2015/0133802 A1 | 5/2015 | Nabutovsky et al. | |
| 2015/0141765 A1 | 5/2015 | Razavi et al. | |
| 2015/0141858 A1 | 5/2015 | Razavi et al. | |

FOREIGN PATENT DOCUMENTS

| | | |
|---|---|---|
| ER | 1508300 | 2/2005 |
| WO | WO-97/24981 | 7/1997 |
| WO | 2012/090148 | 7/2012 |

OTHER PUBLICATIONS

Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.

Quatember, Bernhard et al., "Geometric Modeling and Motion Analysis of the Epicardial Surface of the Heart", Mathematics and Computers in Simulation, vol. 81, No. 3, pp. 608-622, Nov. 2010.

Segars, W. Paul et al., "A Realistic Spline-Based Dynamic Heart Phantom", IEEE Transactions on Nuclear Science, vol. 46, No. 3, pp. 503-506, Jun. 1999.

* cited by examiner

MULTIPLE SHELL CONSTRUCTION TO EMULATE CHAMBER CONTRACTION WITH A MAPPING SYSTEM

BACKGROUND OF THE INVENTION a. Field of the Invention

The instant invention relates to a system and method for multiple shell construction to emulate chamber contraction with a mapping system.

b. Background Art

Electrophysiology (EP) catheters have been used for an ever-growing number of procedures. For example, catheters have been used for diagnostic, therapeutic, mapping and ablative procedures, to name just a few examples. Typically, a catheter is manipulated through the patient's vasculature and to the intended site, for example, a site within the patient's heart, and carries one or more electrodes, which may be used for mapping, ablation, diagnosis, or other treatments.

In this regard, it is known to provide a catheter navigation and mapping system, as set forth in U.S. Pat. No. 7,263,397 issued to Hauck et al. entitled METHOD AND APPARATUS FOR CATHETER NAVIGATION AND LOCATION AND MAPPING IN THE HEART, assigned to the common assignee of the present invention, and hereby incorporated by reference in its entirety. Hauck et al. generally disclose a medical system for finding and displaying the location of electrodes within the body. Hauck et al. further disclose that a roving electrode is swept around in the heart chamber while the heart is beating, and a large number of electrode locations ("data points") are collected. Such data points are taken at all stages of the heart beat and without regard to the cardiac phase. Since the heart changes shape during contraction only a small number of the points represent the maximum heart volume. Moreover, Hauck et al. teach selecting the most exterior points to create a "shell" representing the shape (geometry and/or volume) of the heart (or chamber thereof) at its maximum size. Once the shell is constructed, collected EP data may be subsequently mapped onto the shell and displayed to a user.

Thus, conventional high density mapping approaches create one static shell that the electrophysiologist may use, among other things, as a reference throughout a procedure such as an ablation procedure. The conventional practice of generating and using a single, static shell is not considered unreasonable inasmuch as in constructing just one shell using only the outermost points of the cloud, the electrophysiologist can be reasonably certain that these points coincide with the endo-cardial wall and not, for example, in a blood pool. However, it would nevertheless be desirable to provide a more realistic representation of the changing volume of a heart chamber as it changes throughout the different phases of the heart beat. For example, a more realistic representation would provide more useful information to the electrophysiologist regarding anatomic markers and whether, during ablation, intended targets have been successfully isolated.

Accordingly, there is therefore a need to minimize or eliminate one or more of the shortcomings set forth above pertaining to single shell construction and use.

BRIEF SUMMARY OF THE INVENTION

One advantage of the invention is that it provides the basis for a more realistic rendering of the heart or chambers thereof. In particular, the invention contemplates that a plurality of sensor locations ("data points") are collected by a localization system, including a respective indication of the cardiac phase during (or at which) each point was acquired. From these data points, a plurality of so-called "shells" are constructed, each shell being an electronic model indicative of the geometry and/or volume of a bodily lumen, such as a chamber of the heart. The plurality of shells, once constructed, may be used for a variety of diagnostic, mapping and/or therapeutic procedures (e.g., played back as per a patient's real-time measured ECG). The multiple shells provide the capability for a more accurate rendering of the geometry and/or size/volume of a heart chamber.

A method of processing information is provided that includes a number of steps. The first step involves collecting, for at least one sensor, a plurality of sensor locations as such sensor is swept within the chamber of a bodily lumen such as the heart of a patient. In one embodiment, the sensor is swept within a heart chamber. The next step involves segregating the collected sensor locations into a plurality of sets based on the phase of the cardiac cycle during (or at which) each of the sensor locations were collected. Each set will thus have a particular phase of the cardiac cycle associated therewith. The next step involves generating, for each set of sensor locations, a respective geometry of the heart chamber during the particular cardiac phase specified for that set of points.

In disclosed embodiments, the sensor may comprise either an electrode (e.g., disposed at a distal end of a catheter) or a coil configured to detect one or more characteristics of a magnetic field. In a still further embodiment, the method includes the further step of determining whether the sensor is in contact with the tissue of the chamber before using the collected point (or points) in the construction of the geometry. In one embodiment where contact is determined electrically, a component of a measured complex impedance (i.e., as measured using the electrode itself) is used to determine the adequacy of the electrode-to-tissue contact.

The foregoing and other aspects, features, details, utilities, and advantages of the present invention will be apparent from reading the following description and claims, and from reviewing the accompanying drawings.

DETAILED DESCRIPTION OF THE INVENTION

Figures 1, 2:
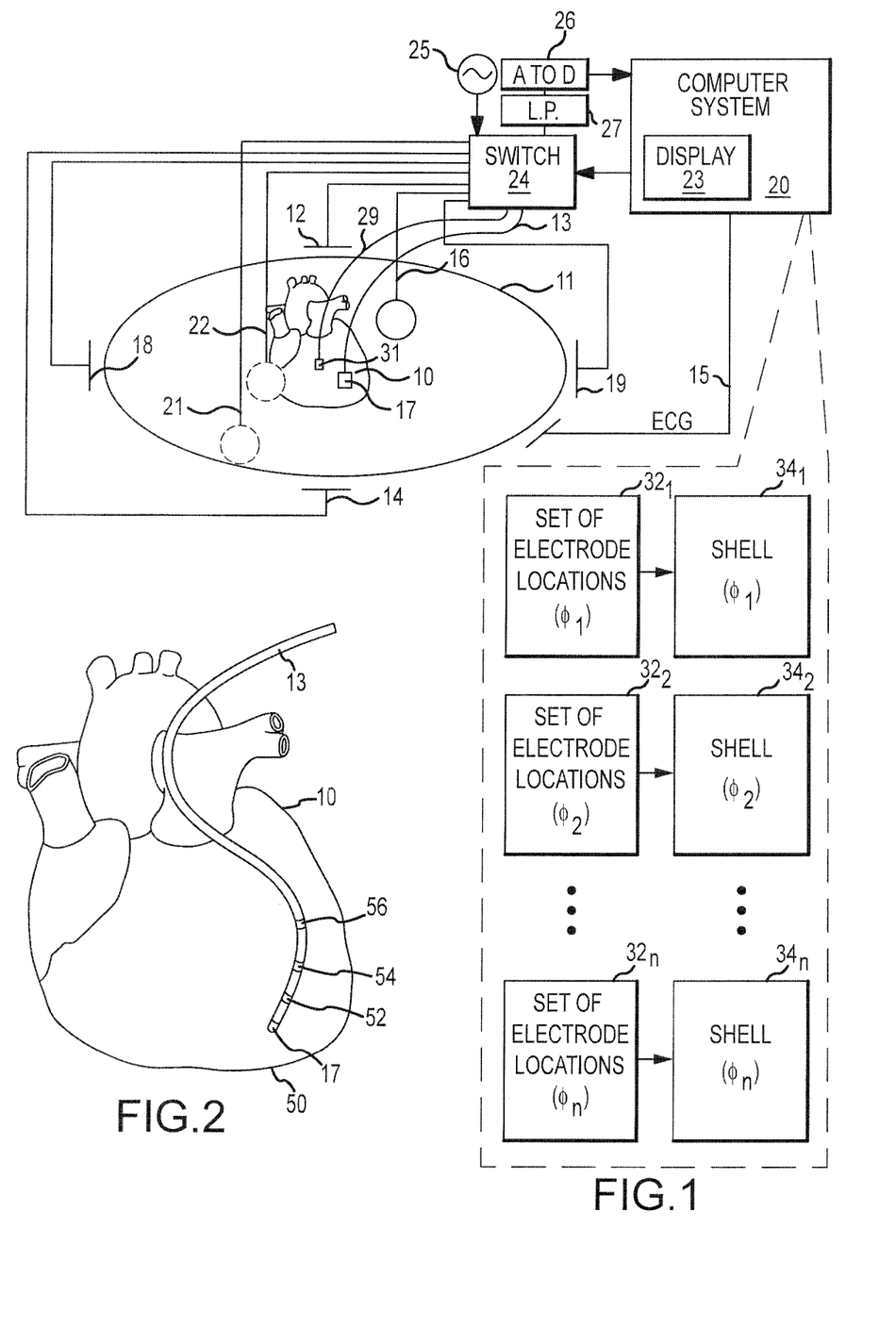
FIG. 1 is a diagrammatic overview of a system in which the present invention may be practiced.
FIG. 2 is diagrammatic view of a catheter (with measurement electrode) in a heart chamber.

Referring now to the drawings wherein like reference numerals are used to identify identical components in the various views, FIG. 1 is a diagrammatic overview of a catheter system in which the invention may be practiced. The system may comprise various visualization, mapping and navigation components as known in the art, including among others, for example, an EnSite™ Electro Anatomical Mapping System commercially available from St. Jude Medical, Inc., or as seen generally by reference to U.S. Pat. No. 7,263,397 entitled "METHOD AND APPARATUS FOR CATHETER NAVIGATION AND LOCATION AND MAPPING IN THE HEART" to Hauck et al., owned by the common assignee of the present invention, and hereby incorporated by reference in its entirety. The system may be used in connection with or for various medical procedures, for example, cardiac ablation procedures (ablation apparatus not shown). It should be understood that embodiments consistent with the invention may, and typically will, include other features not shown or described herein for the sake of brevity and clarity. For example, when used in connection with an ablation catheter, such an ablation catheter may typically include various electrodes (and corresponding leads), a temperature sensor (and corresponding leads), and other features as known in the art.

As described in the Background, conventional visualization/navigation systems use a single, static "shell" to represent the surface geometry and size/volume of the heart (or chamber thereof). One conventional approach to construct such a "shell" is to use the collected electrode locations that correspond to the largest volume of the heart chamber being modeled. As will be described, the invention provides a system and method for constructing not just one but a plurality of shells corresponding to the respective geometry (volume) of the heart chamber of interest as it varies throughout the cardiac cycle. Through this inventive approach, a more realistic rendering may be obtained, particularly as to shape/volume/size.

Referring again to FIG. 1, the catheter system includes a diagrammatic depiction of a heart 10 of a patient 11. The system includes the ability to collect a plurality of catheter locations as the catheter distal end is swept around and within a chamber of the heart. For this purpose, FIG. 1 shows an exemplary catheter localization system of the type based on externally-applied orthogonal electric fields which are used to determine the location of one or more catheter electrodes. Such a system is known generally in the art (e.g., an EnSite NAVX™ Navigation and Visualization System). It should be understood, however, that this embodiment is exemplary only and not limiting in nature. Other technologies for determining the location in 3D space of a catheter may be used in practicing the present invention, including for example, the CARTO navigation and location system of Biosense Webster, Inc., or the AURORA® system of Northern Digital Inc., both of which utilize magnetic fields rather than electrical fields. Accordingly, as used herein, a sensor is provided for producing signals indicative of catheter location information, and may include one or more electrodes, for example in the case of an impedance-based localization system, or alternatively, one or more coils (i.e., wire windings) configured to detect one or more characteristics of a magnetic field, for example in the case of a magnetic-field based localization system.

It should be further understood that in an impedance-based embodiment that is described herein, one or more electrodes may be collectively define the sensor. Such one or more electrodes may be provided on a distal end of a catheter. The localization system may be configured to obtain location information from one or more of the electrodes. The localization system may compute a distal location of the catheter using not only the collected location information, but also a geometrical relationship between the one or more electrodes providing the location information and the distal location on the catheter (e.g., one piece of geometrical information may be the ring electrode to tip distance). Finally, the localization system may use of the computed location as if it were collected directly. Likewise, in a magnetic field based localization embodiment, the catheter tip and the magnetic coil may have a geometrical relationship therebetween where the localization system is configured to use the computed tip location (i.e., computed based on the magnetic coil signals and predefined knowledge of the geometrical relationship between coil and tip) as if such location were collected directly. Of course, other variations are possible.

With continued reference to FIG. 1, in the illustrated impedance-based localization system embodiment, three sets of surface electrodes (patches) are shown: (1) electrodes 12, 14 (X-axis); (2) electrodes 18, 19 (Y-axis); and (3) electrodes 16, 22 (Z-axis). Additionally, a "belly" patch 21 may be used. The surface electrodes are all connected to a switch 24. A representative catheter 13 is shown, which has a single distal electrode 17, which may be referred to herein as a "roving" or "measurement" electrode. The electrode 17 may define the location sensor in this embodiment, but as alluded to above, many variations are possible. FIG. 1 also shows a second, independent catheter 29 with a fixed reference electrode 31, which may be stationary on the heart for calibration purposes. FIG. 1 further shows a computer system 20, a signal generator 25, an analog-to-digital converter 26 and a low-pass filter 27. The computer system 20 includes a processing apparatus configured to perform many of the functions and operations described herein. The computer system 20 is configured to control the signal generator 25 in accordance with predetermined strategies to selectively energize various pairs of surface electrodes, as described in greater detail below. In operation, the computer system 20 is configured to (1) obtain raw patch data (i.e., voltage readings) via the filter 27 and A-D converter 26 and (2) use this raw patch data to determine the raw electrode location coordinates in three-dimensional space (X, Y, Z) of a catheter electrode positioned inside the heart or chamber thereof (e.g., such as the roving electrode 17 mentioned above). Unlike the conventional "shell" construction strategies that collect electrode locations without regard to the phase of the cardiac cycle, the invention contemplates a mechanism to measure or otherwise determine the phase of the patient's cardiac cycle when such electrode location coordinates are being collected. For this purpose, in an embodiment, most or all of the conventional twelve (12) ECG leads, coupled to body surface electrodes and designated collectively by reference numeral 15, are provided to support the acquisition of an electrocardiogram (ECG) of the patient 11. Alternatively, a reference electrode positioned in a fixed location in the heart, such as fixed reference electrode 31, may be used to provide a relatively stable signal indicative of the phase of the heart in the cardiac cycle (e.g., placed at the coronary sinus). More generally, another catheter having an electrode, other than the moving or roving catheter, may be placed and maintained in a constant position relative to the heart to obtain a relatively stable signal indicative of cardiac phase. As shown, the ECG leads 15 are coupled directly to the computer system 20 for acquisition and subsequent processing to obtain the phase of the heart in the cardiac cycle. The ECG leads 15 may be also be provided to other systems (not shown).

Note, the system 20 may employ filtering of the signals appearing on one or more of the ECG leads 15, which filtering may introduce a predetermined amount of delay. For example, in an embodiment operating at 1200 samples/second, a 12-tap digital filter may be used with respect to the ECG-provided signals, which may have the effect of introducing a corresponding twelve time-step delay in the availability of the determined cardiac phase within system 20. In general, the latency in the availability of the cardiac phase data may be acceptable, in view of the resolution of the shell generation. In other words, the relatively low latency in the availability of cardiac phase information may be deemed to have an immaterial impact on the accuracy of the generation of the multiple shells, and the subsequent "playback" of those shells. However, in an alternate embodiment (e.g., for high resolution images of the shells), the generation, use in mapping, "playback" and the like involving the use of the shells/geometries may be adjusted in view of this latency. For example, during generation, the timing of the collected sensor locations and the acquisition of the cardiac phase information may be time synchronized in accordance with the known latency. Likewise, in mapping, the timing of the acquired EP data and cardiac phase information may also be time synchronized in accordance with the known latency. During "playback", the selection of which shell to display may be adjusted based on the measured cardiac phase, in view of this latency. In sum, the patient's ECG can provide the information needed to determine the particular phase of the patient's cardiac cycle at any point in time.

The respective phase information for each sensor (electrode) location will be used to sort the collected data points into groups or sets having a similar (or the same) phase. These groupings are shown generally as sets $32_1, 32_2, \ldots 32_n$, where each set covers an associated phase or phase range $\Phi_1, \Phi_2, \ldots \Phi_n$. Each set $32_i$ can then be used to construct a respective shell, designated $34_1, 34_2, \ldots 34_n$. Each shell $34_i$ has a respective phase $\Phi_1, \Phi_2, \ldots \Phi_n$ associated therewith.

FIG. 2 shows in greater detail an embodiment of the exemplary catheter 13 of FIG. 1. The catheter 13 may be a conventional EP catheter, as shown disposed in the heart 10, for example only, in the left ventricle 50. The EP catheter 13 shown may also include additional ring electrodes 52, 54 and 56. It should be understood that the catheter 13 may include still other electrodes, and in other embodiments such as in EP or RF ablation embodiments, the one or more other electrodes may be used for any number of diagnostic and/or therapeutic purposes. For instance, such electrodes and therefore such catheters may be used for performing ablation procedures, cardiac mapping, electrophysiological (EP) studies and other procedures. The invention is not limited to any one type of catheter or catheter-based system or procedure. In addition, as described above, the location sensor, in the described impedance-based localization embodiment, may comprise one or more of the catheter tip electrode and ring electrodes. All location information may be used to improve the determination of a location data point for use in shell construction.

Before proceeding to a detailed description of multiple shell construction, and to ensure appropriate context, a brief overview of one single shell construction approach will be set forth (FIGS. 3-6).

Figure 3:
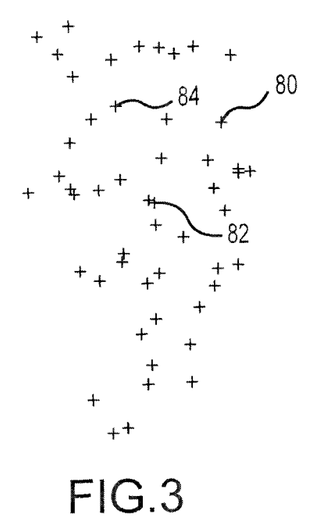
FIG. 3 is a diagrammatic view of a plurality of data points corresponding to collected electrode locations.

FIG. 3 is a graphical representation of the results of sensor location measurements made in the heart. As noted above, a specific location sensor, for example, the roving electrode 17, may be placed on a catheter that is swept around and within the interior of the heart (or chamber thereof) by the physician or other practitioner. The location of this roving electrode is monitored continuously by the localization system described above in connection with FIG. 1. As a result, a plurality of sensor locations are collected over time, which may be thought of as forming a "cloud" of data points. For example, three data points 80, 82 and 84 are called out specifically in FIG. 3. FIG. 3 shows a three dimensional cloud of data points representing the collected location data (i.e., each data point defined by an (X, Y, Z) coordinate).

Figure 4:
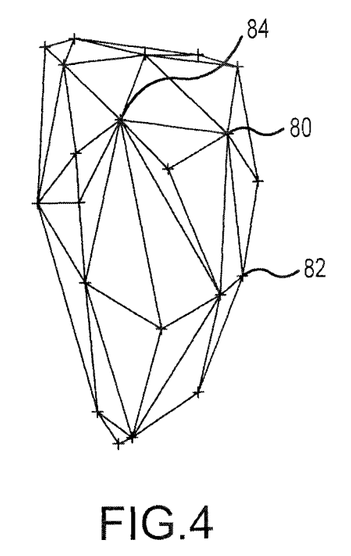
FIG. 4 is a diagrammatic view of a convex hull corresponding to a heart surface.

FIG. 4 is a convex hull shape computed for the cloud of data points represented in FIG. 3. A mathematical algorithm, such as a convex hull algorithm, is used to construct a surface surrounding this cloud of collected electrode locations. The quality of the shell model or its accuracy depends upon both the accuracy of the location algorithm as well as the number of data points collected. Typically, the hull may be composed of triangular panels. Convex hull algorithms are well known and publicly available software packages are available to perform the required calculations/transformations.

Figure 5:
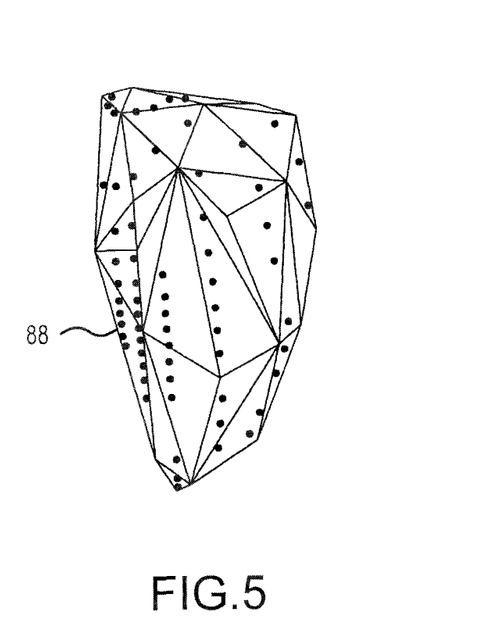
FIG. 5 is a diagrammatic view of a re-sampled convex hull surface.

FIG. 5 shows a re-sampling process carried out on a regular grid to increase the number of points for further computation. The re-sampling process interpolates between vertices on the exterior of the polygon. In essence, intermediate points are defined within each facet of the hull or polyhedron as represented by data point 88. Although the re-sampling process creates interpolated points, these points are nonetheless useful in the smoothing operation shown in FIG. 6.

Figure 6:
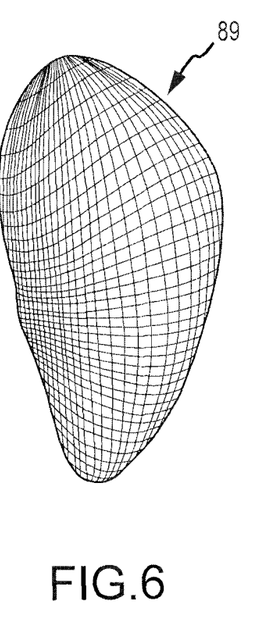
FIG. 6 is a diagrammatic view of a smoothed, computed heart surface.

FIG. 6 shows a smoothed shape 89, which represents a more realistic contour than a polyhedron. This surface may be computed by fitting smooth curves to the enlarged or enhanced data set generated by the re-sampling process. Conventional smoothing algorithms may be used, for example, such as those corresponding to a least squares fit approach. The exterior shell is referred to throughout the specification as the geometry of the chamber.

The known general approach involves the processing of electrode locations (data points) that were collected without regard to the phase of the patient's cardiac cycle at which they were collected. As described above, in one approach it is assumed that the most exterior points that were collected correspond to the diastole portion of the cardiac phase. Conventional shell construction strategies thus prefer/use the most exterior points in building a single shell representing the geometry/volume of the heart chamber. This approach is not necessarily unreasonable since it helps the physician viewing the catheter in relation to the constructed shell to ensure that the catheter is in contact or close to contact with tissue, for example during an ablation procedure. It is nonetheless desirable to increase the accuracy of the rendering of the heart chamber throughout the various phases of the cardiac cycle of the patient. Accordingly, the invention provides for phase-based sensor location collection, which enables the construction of multiple shells in accordance with phase. Each of the shells will have their greatest accuracy at the particular phase of the patient's cardiac cycle at which the underlying data points were collected.

Figure 7:
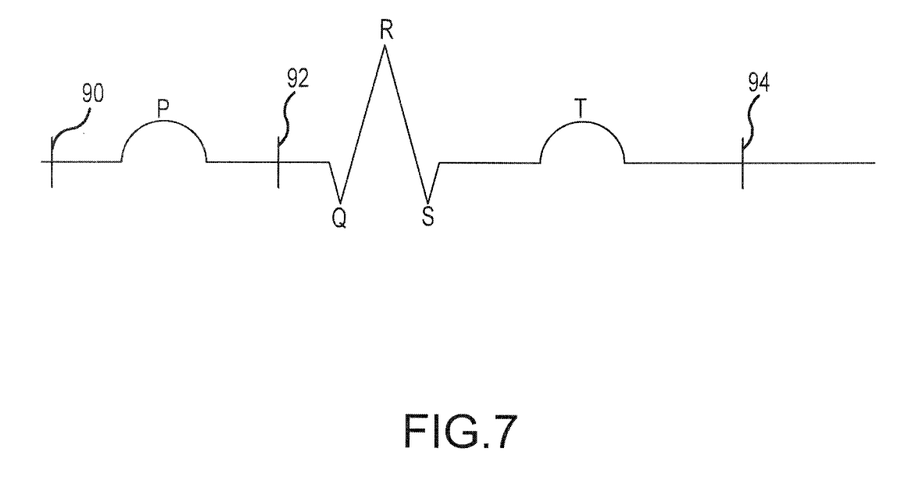
FIG. 7 is a simplified, diagrammatic timing diagram of an electro-cardiogram (ECG) showing various phases of the cardiac cycle.

FIG. 7 is a timing diagram of an electro-cardiogram (ECG) showing various phases of a patient's cardiac cycle. Variations in the volume/geometry will occur throughout the various phases of the cardiac cycle. While the left atrium will be used in this example, it should be understood that other heart chambers (or other bodily lumens) may be characterized through the present invention. When referring to data points, it should be understood that this term refers to collected location coordinates, which can be collected via any means known to one of ordinary skill in the art, including via impedance mapping with an electrode or magnetic mapping with a coil sensor.

At time 90, the left atrium would be at its maximum volume. The shell that is constructed based on the data points collected at this time would have the greatest volume. Electrically speaking, after time 90 on the ECG, a so-called P wave is shown. Atrial systole is the contraction of the heart muscle (myocardia) that is instituted with the onset of the P wave. Thus, after the P wave, for example at time 92, the left atrium would be contracted (systole) and at its minimum volume. The shell constructed for this point would be smaller than that created from the data points collected at time 90. For data points collected between times 90 and 92, the one or more shells that are constructed would show a gradient of the volume change of the left atrium, corresponding to the mechanical contraction that occurs due to the P wave. At time 94, the left atrium would be in a relaxed state, but not yet completely filled with blood. The one or more shells constructed between times 92 and 94 would show the volume increase as the myocardium relaxes. The one or more shells constructed after time 94 would also show a volume increase as the chamber (left atrium) is filled with blood. It should be understood that the collection of sensor location coordinates and the subsequent shell construction can be arranged to occur with and are keyed to the patient's cardiac phase.

Figure 8:
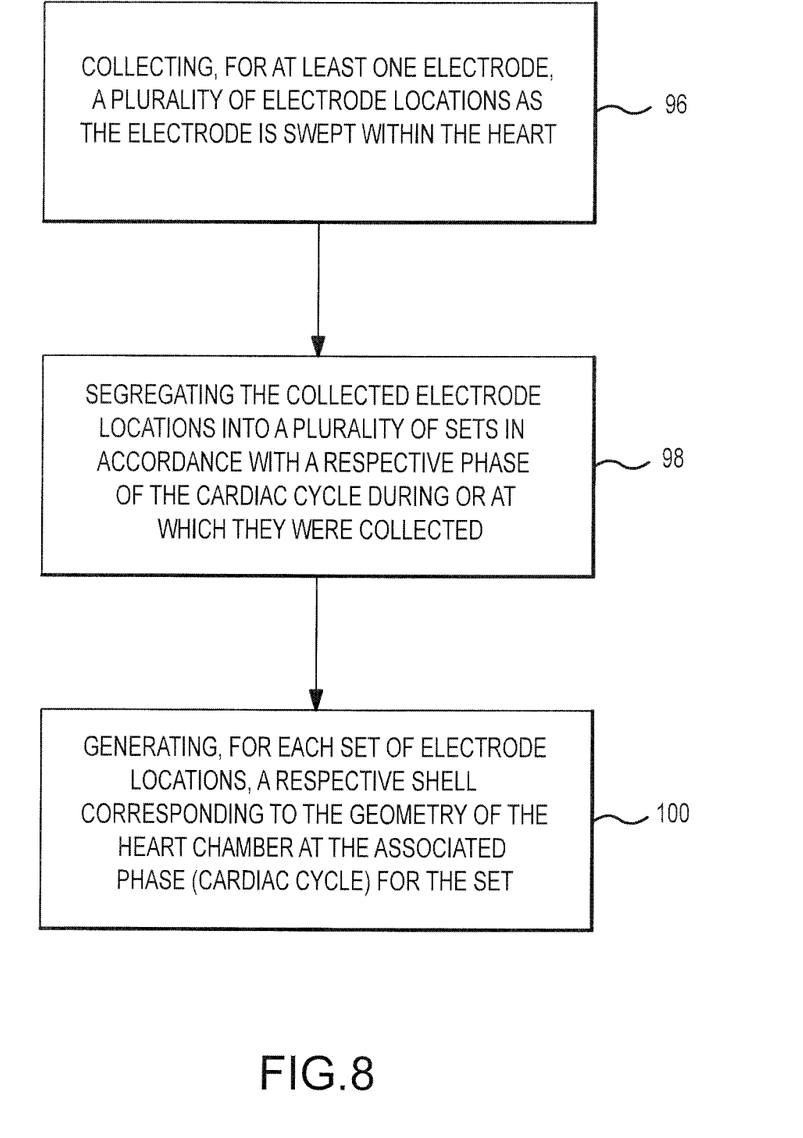
FIG. 8 is a flowchart diagram showing a method of constructing multiple geometries (shells) according to the invention.

FIG. 8 is a flowchart diagram showing a method of constructing multiple shells according to an impedance-based localization embodiment of the invention. It should be understood, as described above, that the principles described herein may be extended to other embodiments based on other technologies for catheter localization (e.g., magnetic field detection based). The method of this embodiment of the invention includes a number of steps, which are designated steps 96, 98 and 100.

In step 96, the method involves collecting, for at least one sensor (electrode), a plurality of locations (data points) as such sensor is swept around and within the heart or chamber thereof. This step may be performed using the system described above in connection with FIG. 1. The collecting step may include the sub-step of determining the particular phase of the cardiac cycle at which each sensor location (data point) is collected. This sub-step may be performed by reference to the conventional ECG signal that is typically monitored, from which the particular phase of the cardiac cycle may be directly measured or derived. In this regard, the invention, in one embodiment, contemplates that different ECG leads (signals defining electrograms) may be selected for use based on predetermined selection criteria. The predetermined selection criteria may include the target heart chamber for which the geometry/shell is to be created and/or may be based on a disease state of the patient's heart. For example only, if there is A-V are not synced, then one of the precordial leads of the ECG may be used when mapping the ventricles since there is little atrial information there to disturb the algorithm.

The collecting step 96 may further include the sub-step of determining whether the sensor (electrode) is in adequate contact with the tissue of the heart chamber so as to qualify that collected data point as reliable. Reliability may be assessed for the purpose of using the data in constructing a shell representing the geometry of the heart or chamber thereof. Although the sub-step of determining adequate contact in the context of an electrode will be described below in connection with FIGS. 9A-9B, in an alternate embodiment, where adequate contact may not be verified for all or at least some of the collected data points, the method may involve selecting or otherwise identifying the outermost data points collected at a particular cardiac phase, and then using those points for shell construction. It should be appreciated that in the Background art, the use of the identified outermost points for purposes of shell construction was done without regard for the particular cardiac phase at which such points were collected. Here, in this alternate embodiment, identification and use of the outmost points is done for specific phases.

Figure 9A:
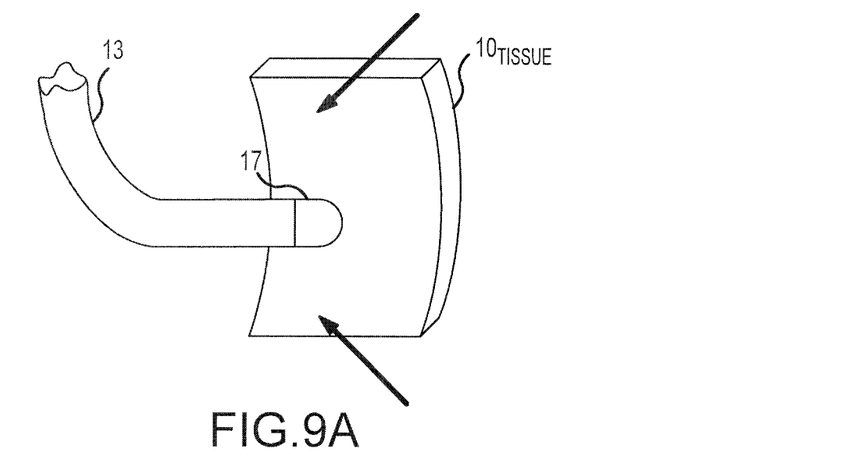
FIGS. 9A-9B are diagrammatic views of one embodiment where a sensor, such as an electrode, is in contact with, and alternatively not in contact with, cardiac tissue.
Figure 9B:
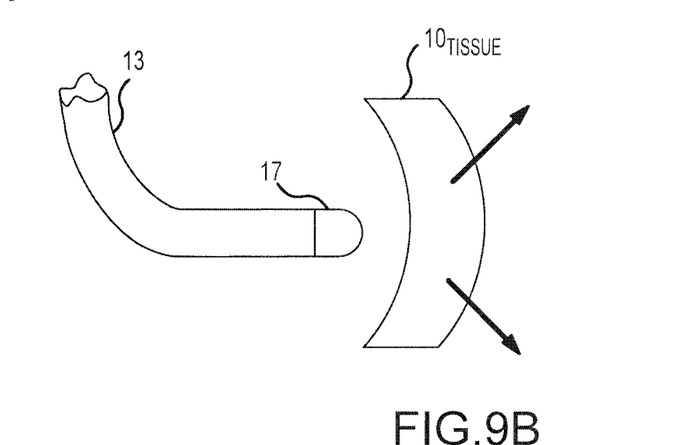

FIGS. 9A-9B are views of a measurement electrode in contact with, and not in contact with, cardiac tissue. These views will be used to describe in greater detail the sub-step of determining adequate contact.

FIG. 9A in particular shows the sensor (tip electrode 17) of the catheter 13 pressed up against and contacting cardiac tissue $10_{TISSUE}$. The invention may use any one or more of a wide variety of electrical-based, electro-mechanical based, force based, optically based, as well as other technology-based approaches known in the art for determining when the electrode is in adequate contact with the tissue. Alternatively, the invention may use an approach for assessing the degree of electrical coupling, for example as expressed in an electrical coupling index (ECI) between such an electrode and tissue, as seen by reference to U.S. patent application Ser. No. 12/253, 637, filed Oct. 17, 2008, entitled "SYSTEM AND METHOD FOR ASSESSING COUPLING BETWEEN AN ELECTRODE AND TISSUE", owned by the common assignee of the present invention, and the disclosure of which is hereby incorporated herein in its entirety.

In one embodiment, an electrically-measured parameter indicative of tissue contact may be used to determine when the sensor (tip electrode 17) is in adequate contact with the cardiac tissue rather than, for example only, located in a blood pool. In an embodiment, a phase angle component of a measured complex impedance may be used as the parameter indicative of contact. Determining the phase angle may involve the sub-steps of supplying an excitation signal to the measurement electrode; sensing the induced signal that occurs as a result of the excitation signal; measuring a complex impedance between the measurement electrode and a second electrode (e.g., a patch electrode based on the excitation and induced signals); and finally, calculating the phase angle of the complex impedance. One phase angle measurement may be as described in U.S. patent application Ser. No. 11/966,232 filed Dec. 28, 2007 entitled SYSTEM AND METHOD FOR MEASUREMENT OF AN IMPEDANCE USING A CATHETER SUCH AS AN ABLATION CATHETER, owned by the common assignee of the present invention, and hereby incorporated by reference in its entirety.

Figure 10:
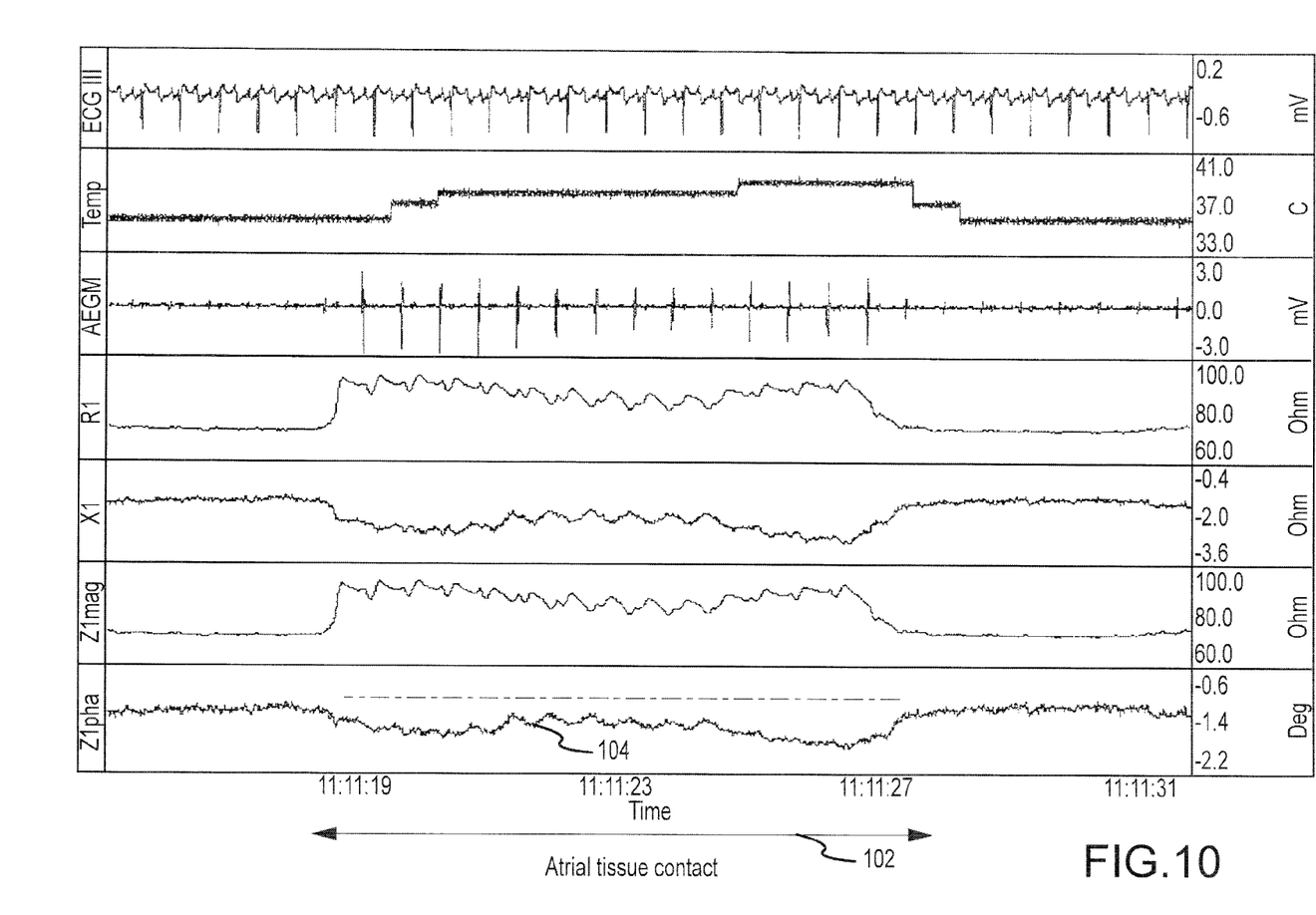
FIG. 10 is a simplified timing diagram showing, in one embodiment, how a computed phase angle component of a measured complex impedance can be used to determine the adequacy of contact between an electrode and tissue.

FIG. 10 is a timing diagram showing, for one embodiment, how a computed phase angle may be used to determine the adequacy of electrode-to-tissue contact. As shown graphically in FIG. 10, during a time period 102 of atrial tissue contact by the sensor (electrode), the determined phase angle component of the measured complex impedance may become more negative, at least sufficiently more negative so as to distinguish between contact and no contact. Alternatively, as described above, an electrical coupling index (ECI) may be used to assess the adequacy of the electrode-to-tissue contact, for purposes of using the point in the shell calculations.

Referring back to FIG. 9B, there are situations where the electrode (e.g., tip electrode 17) is not in contact with the tissue. In an embodiment, the location (data point) collected at that time is preferably not considered to be a part of the outermost shell. As shown in FIG. 9B, as the chamber ($10_{TISSUE}$) expands, in this example, the measurement electrode 17 may no longer remain in contact with the chamber wall. The phase angle or other metric used to determine contact would indicate that the location data point collected at this time (or multiple location data points if multiple ones were collected) is not at the wall. It should be understood, however, as described above, that in alternate embodiments, tissue contact is not required and the method may be configured to use outermost data points.

With continued reference to FIG. 8, the method continues in step 98. In step 98 the method involves segregating or otherwise grouping the collected sensor locations into a plurality of sets based on the respective phase of the cardiac cycle during (or at which) each sensor location was collected. For example, these sets are shown in FIG. 1 as sets $32_1$, $32_2$, ..., $32_n$. Post-grouping, each set $32_i$ of sensor locations has associated therewith a particular phase of the cardiac cycle. It should be understood that "phase" here may in fact cover a range or interval of time of the patient's ECG, and is not necessarily a precise point (value) during the cycle. The size of the particular range or interval may be inversely proportional to the number of shells to be constructed directly from the collected data points. The method then proceeds to step 100.

In step 100, the method involves generating, for each set of sensor locations, a respective shell corresponding to the geometry of the heart chamber at the particular phase associated with that set. For example, these shells are shown in FIG. 1 as shells $34_1$, $34_2$, ... $34_n$. For the construction of the multiple shells, this step may be performed in a conventional manner, for example, each shell as described above in connection with FIGS. 3-6. Each shell has a respective phase associated therewith, as also shown in FIG. 1.

Figure 11:
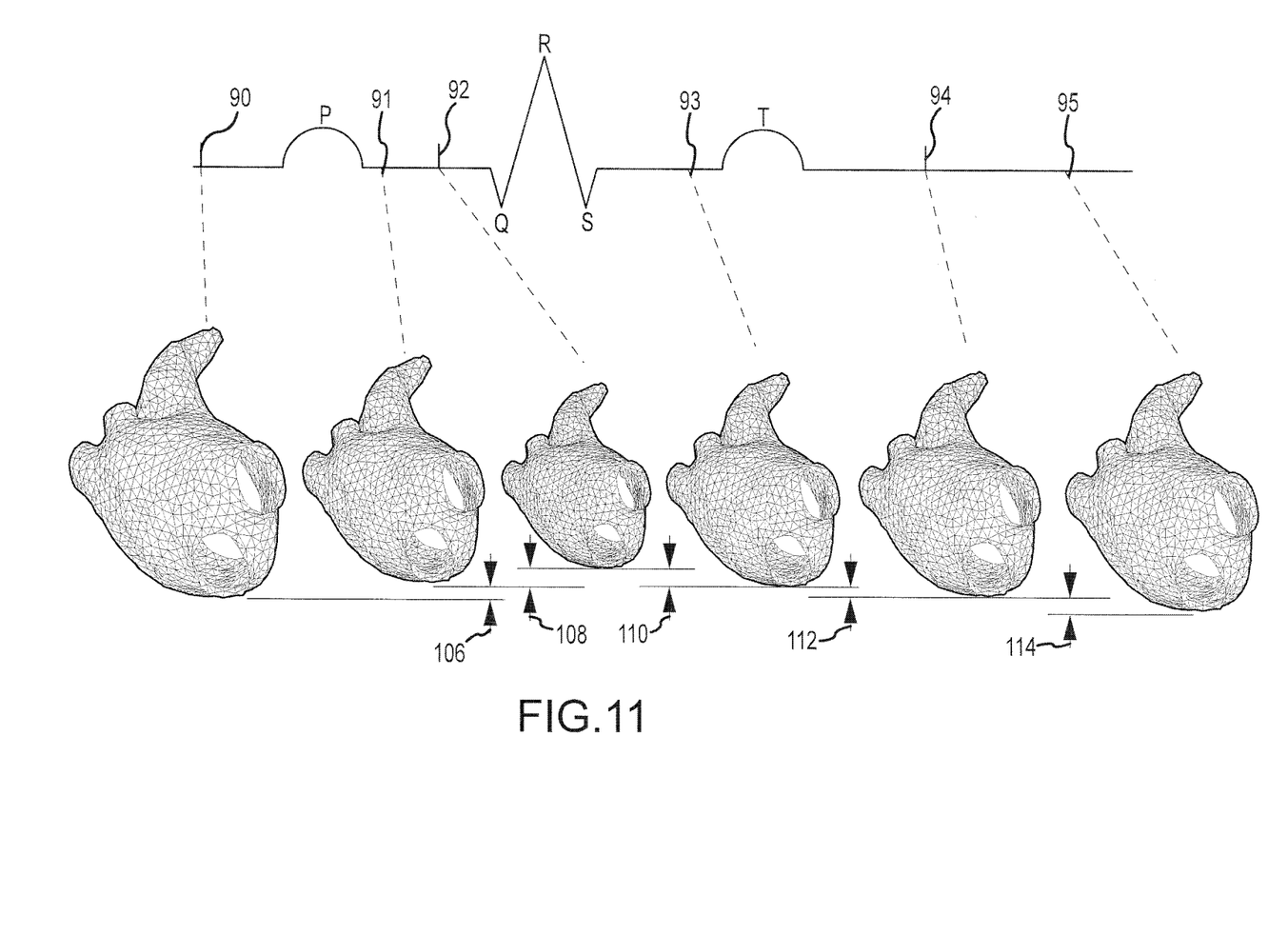
FIG. 11 is a diagrammatic view showing a plurality of constructed geometries corresponding to the varying volumes, as keyed to a patient's ECG.

FIG. 11 is a diagrammatic view showing a plurality of constructed shells having varying volumes, keyed to the phase of a patient's cardiac cycle. It should be understood that FIG. 11 includes a plurality of views of the heart, with particular emphasis on the left atrium, and that the particular variations shown in geometry and/or size are exaggerated throughout the cardiac cycle to more clearly illustrate the invention.

As shown at time 90, the left atrium would be at its maximum volume. After time 90 on the ECG, the P wave is shown. After the P wave (electrical), the left atrium will begin to contract. At time 91, the amount of contraction is indicated by a first arbitrary amount 106. Further contraction occurs through a second arbitrary amount 108 until, for example, about time 92, when the left atrium would be contracted (systole) and at its minimum volume. The shell constructed for this point would be smaller than a shell created from points collected at time 90. For points collected between times 90 and 92, the respective shells (not shown other than for time 91) that are constructed would show a gradient of the volume change in the left atrium, corresponding to the mechanical contraction that occurs due to the P wave.

At time 94, the left atrium would be in a relaxed state, but not yet completely filled with blood. Shells constructed between times 92 and 94, for example at time 93 would show the volume increase (e.g., by a third arbitrary amount 110) as the myocardium relaxes. The shell for time 94 shows an additional increase compared to the shell at time 93 by a fourth arbitrary amount 112. The shells constructed after time 94, for example at time 95, would show a still further volume increase as the chamber (left atrium) continues to be filled with blood. Such increase is shown by a fifth arbitrary amount 114.

Once the shells have been constructed, they can be played-back (e.g., sequentially reconstructed and displayed on display 23) in accordance with the real-time measurement of the patient's ECG. The processing apparatus of computer system 20 may be further configured to superimpose a representation of a catheter on the sequential display of the plurality of shells/geometries. For example, such a catheter may be an ablation catheter, and the superimposing being performed during the course of a medical procedure on the patient. Still further, the processing apparatus of the computer system 20 may be further configured to track movement of the catheter, through its localization functionality described above, where the movement of the catheter, as represented by it continuously updated location, is synchronized to the display of the plurality of shells/geometries. Through this operation, the dithering appearance of the catheter can be matched to the movement of the heart (or chamber/wall thereof). Still further, that the computer system 20 may be configured to allow the shells/geometries to be updated over time. For example, the user (e.g., physician) can return to a "build" mode to collect new data points, which can be used to supplement or replace existing data. Finally, the computer system 20 may be configured, in a still further alternate embodiment, to smoothly interpolate between shells constructed from measured data points, so as to increase the total number of shells for subsequent display, which reduce the impression jerky or stuttered changing size/volumes over time. It should be understood that these functions are exemplary only and not limiting in nature.

Of course, various EP data may be mapped onto such shells, and such shells may be used in aid of catheter navigation, and in many other ways know known or hereinafter developed in the art. Such EP data may, for example, comprise cardiac physiological electrical potentials representing activity.

In a further embodiment, the invention provides a mechanism to track a point at the same anatomic location throughout the mechanical contraction during the cardiac cycle. In alternate embodiments, a plurality of individual points may be so tracked. This permits, for example, mapping activation potentials on the diastolic (i.e., maximum volume) shell despite the electrical activation having occurred during systole. This may be accomplished by mapping the voltage levels recorded during systole to the same anatomic point in diastole, despite the fact that the coordinate of that point, taken relative to a reference coordinate system origin, will have changed over time owing to the movement of the cardiac wall during the course of the contraction cycle. This embodiment may be used for visualizing data throughout the mechanical cycle even though the data being displayed is particular to one phase of the mechanical cycle.

One approach that may be used to implement feature of the invention involves the use of known regression algorithms which for this feature of the invention are configured to relate the surfaces of the various shells as the respective sizes change during the cardiac cycle. For example, such an algorithm may be configured to determine an optimum least squares regression as you trace the same point (i.e., in this case the same anatomic location) between the various-sized shells (i.e., the various sizes shown in FIG. 11). This approach can provide adequate accuracy for the mapping purpose described above.

While the present invention may be used to provide a plurality of different shell constructions, in accordance with the phase of the cardiac cycle, it should be understood that a wide variety of technologies for determining a catheter electrode location may be used, one exemplary technology (e.g., EnSite™ Electro Anatomical Mapping System based) being shown and described in connection with FIG. 1. To ensure that one of ordinary skill in the art may easily practice the invention, a more detailed description of the electrode localization system of FIG. 1 will now be made. It bears emphasizing that the following detailed description is not intended to be limiting as to the range and variety of structures that can be used to practice the invention.

Referring again to FIG. 1, each patch electrode is coupled to the switch 24 and pairs of electrodes are selected by software running on the computer 20, which couples the patches to the signal generator 25. A pair of electrodes, for example electrodes 18 and 19, are excited by the signal generator 25 and they generate a field in the body of the patient 11 and the heart 10. During the delivery of the current pulse, the remaining patch electrodes may be referenced to the belly patch 21 and the voltages impressed on these remaining electrodes are measured by the A-to-D converter 26. Suitable low-pass filtering of the digital data is subsequently performed in software to remove electronic noise and cardiac motion artifacts after suitable low pass filtering in filter 27. In this fashion, the surface patch electrodes are divided into driven and non-driven electrode sets. While a pair of electrodes are driven by the current generator 25 the remaining non-driven electrodes may be used as references to synthesize the orthogonal drive axes.

The belly patch electrode 21 seen in the figure is an alternative to a fixed intra-cardiac electrode 31. In many instances a coronary sinus electrode or other fixed electrode in the heart can be used as a reference for measuring voltages and displacements. All of the raw patch voltage data is measured by the A-to-D converter 26 and may be stored in the computer under the direction of control software. This electrode excitation process occurs rapidly and sequentially as alternate sets of patch electrodes are selected and the remaining members of the set are used to measure voltages. This collection of voltage measurements is referred to herein as the "patch data set". The software has access to each individual voltage measurement made at each patch during each excitation of each pair of electrodes.

The raw patch data is used to determine the "raw" electrode locations in three dimensional space (X,Y,Z) of the electrodes inside the heart, such as the roving electrode 17.

If the sensor (roving electrode 17) is swept around and within the heart chamber while the heart is beating a large number of location data points are collected. The location attributes of the sensor within the heart are measured while the electric field is established the heart by the surface patch electrodes. According to the invention, the phase of the cardiac cycle is also measured and stored along with each location data point.

It should be understood that the system 20 as described above may include conventional processing apparatus known in the art, capable of executing pre-programmed instructions stored in an associated memory, all performing in accordance with the functionality described herein. It is contemplated that the methods described herein, including without limitation the method steps of FIG. 8, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of processing information, comprising the steps of:
    collecting, for at least one sensor, a plurality of sensor locations as the at least one sensor is swept within a heart chamber of a patient;
    segregating, using a computer processing apparatus, the collected sensor locations into a plurality of sets in accordance with a respective phase of a cardiac cycle during or at which each sensor location was collected, each set having associated therewith a predetermined phase of the cardiac cycle; and
    generating, for each set, a respective geometry of the heart chamber at the associated phase of the cardiac cycle, wherein a first geometry of the plurality of geometries is generated exclusively from a first set of said plurality of sets and a second geometry of the plurality of geometries is generated exclusively from a second set of said plurality of sets, said second set being different from said first set such that sensor locations in said first set are distinct from sensor locations in said second set, the sensor locations in said first set being associated with a first phase of the cardiac cycle during or at which said sensor locations in said first set were collected and the sensor locations in said second set being associated with a second phase of the cardiac cycle during or at which said sensor locations in said second set were collected, wherein said first phase is different from said second phase, and wherein said first phase comprises a first range of phase values and said second phase comprises a second range of phase values different from and non-overlapping with respect to said first range of phase values such that sensor locations in said first set are distinct from sensor locations in said second set by virtue of at least the phase of the cardiac cycle during or at which respective sensor locations were collected.

2. The method of claim 1 further including the step of:
    determining if the sensor is in contact with tissue of the heart chamber.

3. The method of claim 2 further comprising the step of forming the sensor by providing a coil configured to detect a magnetic field.

4. The method of claim 3 wherein said forming step further includes the sub-step of providing a catheter with a distal tip electrode wherein the sensor magnetic coil and the distal tip electrode have a geometrical relationship therebetween, and wherein said generating step includes the substep of computing, for at least one of the sets containing phase-associated sensor locations, a plurality of distal tip locations using the sensor locations in accordance with the geometrical relationship.

5. The method of claim 2 further comprising the step of forming the sensor by providing an electrode.

6. The method of claim 5 wherein said determining tissue contact step includes the substeps of:
supplying an excitation signal to the electrode;
measuring a complex impedance of the tissue proximate the electrode; and
determining when the electrode is in contact with the tissue when a component of the measured complex impedance meets predetermined criteria.

7. The method of claim 6 wherein said step of measuring the complex impedance includes the sub-step of sensing an induced signal produced in response to the excitation signal between the electrode and a patch affixed to the patient.

8. The method of claim 7 wherein the sub-step of sensing the induced signal includes measuring the induced signal between the electrode and a patch affixed to the patient.

9. The method of claim 5 wherein said generating step includes the substeps of:
qualifying locations that have been determined to have been collected when the electrode was in contact with tissue of the heart chamber; and
constructing the respective geometries using qualified electrode locations.

10. The method of claim 1 further including the step of:
displaying the plurality of geometries in accordance with a measured phase of the patient's cardiac cycle.

11. The method of claim 10 further including the steps of:
acquiring electrophysiologic (EP) data associated with the heart chamber; and
mapping the acquired EP data on the plurality of geometries.

12. The method of claim 11 wherein said EP data comprises electrical activation potential values corresponding to physiological electrical activity.

13. The method of claim 12 wherein the step of acquiring EP data includes the sub-step of acquiring an EP data point at the first phase of the cardiac cycle, and wherein said mapping step includes the sub-step of associating the acquired EP data point to the same anatomic location on both a first one of the geometries corresponding to the first phase and on a second one of the geometries corresponding to the second phase of the cardiac cycle different from the first phase.

14. The method of claim 13 further comprising the steps of:
determining respective positions on the first and second geometries that define the same anatomic location; and
mapping the acquired EP data point to the respective positions.

15. The method of claim 14 wherein said step of determining respective positions include the sub-step of:
defining a least squares regression through corresponding points in said shells.

16. The method of claim 1 further including the steps of:
acquiring cardiac phase information; and
associating the acquired cardiac phase information with the collected sensor locations by synchronizing the respective times during or at which the sensor locations were collected and the phase information was acquired.

17. The method of claim 16 wherein said acquiring step includes the substeps of:
providing a plurality of body surface electrodes on the patient for acquiring respective body surface electrograms;
selecting one or more of the body surface electrograms in accordance with predetermined selection criteria;
processing the selected body surface electrograms to obtain the cardiac phase.

18. The method of claim 17 wherein the predetermined selection criteria includes at least one from the group comprising a target heart chamber whose geometry is to be determined and a disease state of the patient's heart.

19. The method of claim 16 wherein said acquiring step includes the substep of:
providing a reference electrode fixed in location in the heart configured to produce a signal indicative of the phase of the cardiac cycle.

20. The method of claim 1 wherein said segregating step comprises the substep of:
identifying, for each cardiac phase for which a set is to be produced, the outermost collected sensor locations.

21. The method of claim 1 further comprising the steps of:
forming the sensor by providing a plurality of electrodes on a distal end of a catheter;
obtaining location information from one or more of the electrodes;
computing a distal location of the catheter using the collected location information in accordance with a geometrical relationship between the one or more electrodes from which location information is obtained and the distal location of the catheter; and
defining the collected sensor location as corresponding to the computed distal location of the catheter.

22. The method of claim 1 wherein said generating step further includes generating said first geometry according to a geometry construction strategy and generating said second geometry according to said geometry construction strategy.

23. The method of claim 1 further including the steps of:
providing a plurality of body surface electrodes on the patient for acquiring respective body surface electrograms;
selecting one or more of the body surface electrograms in accordance with a disease state of the patient's heart;
determining the phase of the cardiac cycle of the patient by processing the selected body surface electrograms; and
associating the collected sensor locations with the determined phase of the cardiac cycle during or at which each sensor location was collected.

24. A system for processing information, comprising:
means for collecting, for at least one sensor, a plurality of sensor locations as the at least one sensor is swept within a heart chamber of a patient;
means, including a computer processing apparatus, for segregating the collected sensor locations into a plurality of sets in accordance with a respective phase of a cardiac cycle during or at which each sensor location was collected, each set having associated therewith a predetermined phase of the cardiac cycle; and
means for generating, for each set, a respective geometry of the heart chamber at the associated phase of the cardiac cycle, wherein a first geometry of the plurality of geometries is generated exclusively from a first set of said plurality of sets and a second geometry of the plurality of geometries is generated exclusively from a second set of said plurality of sets, said second set being different from said first set such that sensor locations in said first set are distinct from sensor locations in said second set, the sensor locations in said first set being associated with a first phase of the cardiac cycle during or at which said sensor locations in said first set were collected and the sensor locations in said second set being associated with a second phase of the cardiac cycle during or at which said sensor locations in said second set were collected, wherein said first phase is different from said second phase, and wherein said first phase comprises a first range of phase values and said second phase comprises a second range of phase values different from and non-overlapping with respect to said first range of phase values such that sensor locations in said first set are distinct from sensor locations in said second set by virtue of at least the phase of the cardiac cycle during or at which respective sensor locations were collected.

25. A system for processing information, comprising:
a processing apparatus configured to collect, for at least one sensor, a plurality of sensor locations as the at least one sensor is swept within a heart chamber of a patient, said processing apparatus being further configured to segregate the collected sensor locations into a plurality of sets in accordance with a respective phase of a cardiac cycle during or at which each sensor location was collected, each set having associated therewith a predetermined phase of the cardiac cycle, said apparatus being further configured to generate, for each set, a respective geometry of the heart chamber at the associated phase of the cardiac cycle, wherein a first geometry of the plurality of geometries is generated exclusively from a first set of said plurality of sets and a second geometry of the plurality of geometries is generated exclusively from a second set of said plurality of sets, said second set being different from said first set such that sensor locations in said first set are distinct from sensor locations in said second set, the sensor locations in said first set being associated with a first phase of the cardiac cycle during or at which said sensor locations in said first set were collected and the sensor locations in said second set being associated with a second phase of the cardiac cycle during or at which said sensor locations in said second set were collected, wherein said first phase is different from said second phase, and wherein said first phase comprises a first range of phase values and said second phase comprises a second range of phase values different from and non-overlapping with respect to said first range of phase values such that sensor locations in said first set are distinct from sensor locations in said second set by virtue of at least the phase of the cardiac cycle during or at which respective sensor locations were collected.

26. The system of claim 25 further including a display, said processing apparatus being further configured to display the plurality of geometries in accordance with a measured phase of the patient's cardiac cycle.

27. The system of claim 26 wherein said processing apparatus is further configured to superimpose a representation of a catheter on said display of the plurality of geometries.

28. The system of claim 27 wherein said processing apparatus is further configured to track movement of the catheter, said processing apparatus being further configured to synchronize the movement of the catheter to the display of the plurality of geometries.

29. The system of claim 25 further including the steps of:
acquiring electrophysiologic (EP) data associated with the heart chamber; and
mapping the acquired EP data on the plurality of geometries.

30. The system of claim 29 wherein said EP data comprises electrical activation potential values corresponding to physiological electrical activity.

* * * * *